United States Patent
Hori et al.

(10) Patent No.: US 10,731,009 B2
(45) Date of Patent: Aug. 4, 2020

(54) CURED SILICONE PARTICLES AND COSMETIC INCORPORATING SAME THEREIN

(71) Applicant: Dow Corning Toray Co., Ltd., Tokyo (JP)

(72) Inventors: Seiji Hori, Chiba (JP); Yasue Kanzaki, Chiba (JP); Yoshitsugu Morita, Chiba (JP); Mari Wakita, Chiba (JP)

(73) Assignee: DOW TORAY CO., LTD., Tokyo (JP)

( * ) Notice: Subject to any disclaimer, the term of this patent is extended or adjusted under 35 U.S.C. 154(b) by 209 days.

(21) Appl. No.: 15/747,149

(22) PCT Filed: Jul. 22, 2016

(86) PCT No.: PCT/JP2016/071626
§ 371 (c)(1),
(2) Date: Jan. 23, 2018

(87) PCT Pub. No.: WO2017/018358
PCT Pub. Date: Feb. 2, 2017

(65) Prior Publication Data
US 2018/0215877 A1  Aug. 2, 2018

(30) Foreign Application Priority Data

Jul. 24, 2015 (JP) ................................ 2015-147252

(51) Int. Cl.

| | | |
|---|---|---|
| *C08G 77/50* | (2006.01) | |
| *A61Q 19/00* | (2006.01) | |
| *A61Q 1/00* | (2006.01) | |
| *A61K 8/02* | (2006.01) | |
| *A61K 8/891* | (2006.01) | |
| *A61Q 17/04* | (2006.01) | |
| *A61Q 1/02* | (2006.01) | |
| *A61Q 19/08* | (2006.01) | |
| *A61Q 5/06* | (2006.01) | |
| *A61K 8/895* | (2006.01) | |
| *A61Q 1/12* | (2006.01) | |
| *A61Q 15/00* | (2006.01) | |
| *C08L 83/04* | (2006.01) | |
| *C09D 183/04* | (2006.01) | |
| *C08G 77/12* | (2006.01) | |
| *C08G 77/20* | (2006.01) | |

(52) U.S. Cl.
CPC ............ *C08G 77/50* (2013.01); *A61K 8/0241* (2013.01); *A61K 8/891* (2013.01); *A61K 8/895* (2013.01); *A61Q 1/00* (2013.01); *A61Q 1/02* (2013.01); *A61Q 1/12* (2013.01); *A61Q 5/06* (2013.01); *A61Q 15/00* (2013.01); *A61Q 17/04* (2013.01); *A61Q 19/00* (2013.01); *A61Q 19/08* (2013.01); *C08L 83/04* (2013.01); *C09D 183/04* (2013.01); *A61K 2800/10* (2013.01); *A61K 2800/412* (2013.01); *A61K 2800/654* (2013.01); *C08G 77/12* (2013.01); *C08G 77/20* (2013.01)

(58) Field of Classification Search
None
See application file for complete search history.

(56) References Cited

U.S. PATENT DOCUMENTS

| | | | |
|---|---|---|---|
| 5,929,162 | A | 7/1999 | Horne et al. |
| 6,291,563 | B1 | 9/2001 | Horne et al. |
| 2015/0189867 | A1 | 7/2015 | Kroupa et al. |

FOREIGN PATENT DOCUMENTS

| | | |
|---|---|---|
| EP | 0516057 A1 | 12/1992 |
| EP | 0829253 A2 | 3/1998 |
| JP | H04348143 A | 12/1992 |
| JP | H04353576 A | 12/1992 |
| JP | H07197815 A | 8/1995 |
| JP | H0885753 A | 4/1996 |
| JP | H0920631 A | 1/1997 |
| JP | 2003226812 A | 8/2003 |
| JP | 2009173694 A | 8/2009 |
| JP | 2009242292 A | 10/2009 |
| JP | 2015113303 A | 6/2015 |
| JP | 2015520291 A | 7/2015 |
| WO | 2014098205 A2 | 6/2014 |
| WO | WO2016100830 A1 | 6/2016 |

OTHER PUBLICATIONS

Machine assisted translation of JP2003226812A obtained from https://worldwide.espacenet.com on Feb. 14, 2019, 34 pages.
Machine assisted translation of JP2009242292A obtained from https://worldwide.espacenet.com on Feb. 14, 2019, 25 pages.
PCT/JP2016/071626 International Search Report dated Oct. 18, 2016, 2 pages.
English language abstract and machine translation for JPH04353576 (A) extracted from http://worldwide.espacenet.com database on Jan. 26 2018, 9 pages.

(Continued)

*Primary Examiner* — Nicole P Babson

(74) *Attorney, Agent, or Firm* — Warner Norcross + Judd LLP

(57) ABSTRACT

Cured silicone particles are disclosed. The cured silicone particles are obtained by curing a curable silicone composition comprising at least components (A) through (C), wherein components (A) and (B) are polyorganosiloxanes having certain average formulas, and component (C) is a catalyst. The average particle size of the cured silicone particles is from 0.1 to 500 μm. Related methods and a cosmetic material comprising the cured silicone particles are also disclosed.

13 Claims, No Drawings

(56) References Cited

OTHER PUBLICATIONS

English language abstract and machine translation for JPH07197815 (A) extracted from http://worldwide.espacenet.com database on Jan. 26, 2018, 7 pages.
English language abstract and machine translation for JPH0885753 (A) extracted from http://worldwide.espacenet.com database on Jan. 26, 2018, 18 pages.
English language abstract and machine translation for JPH0920631 (A) extracted from http://worldwide.espacenet.com database on Jan. 26, 2018, 15 pages.
English language abstract and machine translation for JP2009173694 (A) extracted from http://worldwide.espacenet.com database on Jan. 26, 2018, 37 pages.
English language abstract and machine translation for JP2015113303 (A) extracted from http://worldwide.espacenet.com database on Jan. 26, 2018, 37 pages.

CURED SILICONE PARTICLES AND COSMETIC INCORPORATING SAME THEREIN

CROSS-REFERENCE TO RELATED APPLICATIONS

This application is the National Stage of International Application No. PCT/JP2016/071626 filed on 22 Jul. 2016, which claims priority to and all advantages of Japanese Patent Application No. 2015-147252 filed on 24 Jul. 2015, the content of which is hereby incorporated by reference.

TECHNICAL FIELD

The present invention relates to cured silicone particles with high dispersibility and to a cosmetic material with an excellent usage feeling containing the cured silicone particles.

BACKGROUND ART

The cured silicone particles are used as an additive for cosmetic materials, paints, inks, thermosetting organic resins, thermoplastic organic resins, and the like, and in particular, are preferably used as an internal stress emollient for thermosetting organic resins or as a surface lubricant for organic resin films.

The cured silicone particles are made by curing an addition reaction curable silicone composition or a condensation reaction curable silicone composition, and the particle size differs according to the manufacturing method. Generally, there are limitations to refinement when pulverizing cured material into granular material, and even from an energy cost point of view, a manufacturing method that causes a curing reaction of particulates of the curable silicone composition to provide cured silicone particles with a small particle size is preferable.

However, even if a primary particle is fine, the fine cured particles can easily aggregate to secondary particles, and an aggregate may not easily redisperse to primary particles. This is caused by a phenomenon in which primary particles bond with one another as aggregates, and the bond is difficult to break (dissociate).

There is a problem in which, when cured silicone particles are added to a solvent or the like, the cured silicone particles become secondary aggregates or conglomerates thereof without dispersing at the primary particle size, dispersion is insufficient, and a uniform mixture cannot be prepared, and a composition containing the cured silicone particles cannot sufficiently demonstrate properties of the cured silicone particles. Generally, particles with low hardness such as silicone rubber particulates easily aggregate. Japanese Unexamined Patent Application Publication No. H04-348143 and Japanese Unexamined Patent Application Publication No. H04-353576 respectively propose improving fluidity and dispersibility by attaching inorganic particles to the particle surface of cured silicone particles as a countermeasure. However, there was a problem in which an inorganic feeling of the inorganic particles was transferred to the cured silicone particles.

Japanese Unexamined Patent Application Publication No. H07-197815, Japanese Unexamined Patent Application Publication No. H08-085753, and Japanese Unexamined Patent Application Publication No. H09-020631 respectively propose providing dispersibility and fluidity similar to that of silsesquioxane particulates by attaching silsesquioxane fine particles with high hardness to the particle surface of cured silicone particles. However, there is problem in which the oil absorbing properties of the cured silicone particles are greatly reduced.

Therefore, there is demand for cured silicone particles with weak cohesive properties but high dispersibility, without having to mix a third component such as inorganic fine particles, silsesquioxane particles, or the like.

PRIOR ART DOCUMENTS

Patent Documents

Patent Document 1: Japanese Unexamined Patent Application Publication No. H04-348143
Patent Document 2: Japanese Unexamined Patent Application Publication No. H04-353576
Patent Document 3: Japanese Unexamined Patent Application Publication No. H07-197815
Patent Document 4: Japanese Unexamined Patent Application Publication No. H08-085753
Patent Document 5: Japanese Unexamined Patent Application Publication No. H09-020631

SUMMARY OF THE INVENTION

Problems to be Solved by the Invention

An object of the present invention is to provide cured silicone particles with excellent dispersibility, and to provide a cosmetic material with an excellent usage feeling.

Means for Solving the Problems

The cured silicone particles of the present invention are obtained by curing a curable silicone composition including at least the following components (A) through (C), wherein the average particle size is 0.1 to 500 m:

(A) a polyorganosiloxane expressed by the average formula:

$$[R^a R^b{}_2 SiO(R^b{}_2 SiO)_n]_4 Si$$

(where n is a number that is 0 or higher, however, in one molecule, at least one n is a number that is 1 or higher; $R^a$ may be the same or different, and represents an alkyl group with 1 to 6 carbon atoms, or an alkenyl group with 2 to 12 carbon atoms, however, in one molecule, at least two $R^a$ are alkenyl groups; and $R^b$ may be the same or different, and represents an alkyl group with 1 to 6 carbon atoms, an alkenyl group with 2 to 12 carbon atoms, or an aryl group with 6 to 20 carbon atoms);

(B) (B-1) a polyorganosiloxane expressed by the average unit formula:

$$(R^c{}_3 SiO_{1/2})_p (R^c{}_2 SiO_{2/2})_q (R_d SiO_{3/2})_r$$

(where $R^c$ may be the same or different, and represents an hydrogen atom, an alkyl group with 1 to 6 carbon atoms, or an aryl group with 6 to 20 carbon atoms, however, in one molecule, at least two $R^c$ are hydrogen atoms; and $R^d$ may be the same or different, and represents an alkyl group with 1 to 6 carbon atoms, or an aryl group with 6 to 20 carbon atoms, and p, q, and r are all numbers that are larger than 0 and that satisfy the equation p+q+r=1);

and/or (B-2) a polyorganosiloxane expressed by the average formula $$HR^d{}_2 SiO(R^d{}_2 SiO)_m SiR^d{}_2 H$$

(where m is a number larger than 0, and $R^d$ is the same as described above); and (C) a catalyst for a hydrosilylation reaction.

The method of manufacturing cured silicone particles of the present invention includes: making fine particles from a mixture of the component (A) and the component (B), adding these fine particles to the component (C) to produce fine particles of a curable silicone composition, and then causing a curing reaction of the composition.

Furthermore, the method of manufacturing other cured silicone particles according to the present invention includes: blending the component (A), the component (B), and the component (C), producing fine particles thereof, and then causing a curing reaction of the composition.

Furthermore, the cosmetic material of the present invention contains the aforementioned cured silicone particles.

Effects of the Invention

The cured silicone particles of the present invention have excellent dispersibility in liquids or cosmetic materials, and can enhance the usage feeling of the cosmetic material. Furthermore, the method of manufacturing of the present invention can efficiently manufacture these cured silicone particles. Furthermore, the cosmetic material of the present invention has an excellent usage feeling.

MODE FOR CARRYING OUT THE INVENTION

The cured silicone particles of the present invention are obtained by curing a curable silicone composition including at least the following components (A) through (C), wherein the average particle size is 0.1 to 500 am:

(A) a polyorganosiloxane expressed by the average formula:

[$R^aR^b{}_2SiO(R^b{}_2SiO)_n$]$_4Si$ (where n is a number that is 0 or higher, however, in one molecule, at least one n is a number that is 1 or higher; $R^a$ may be the same or different, and represents an alkyl group with 1 to 6 carbon atoms, or an alkenyl group with 2 to 12 carbon atoms, however, in one molecule, at least two $R^a$ are alkenyl groups; and $R^b$ may be the same or different, and represents an alkyl group with 1 to 6 carbon atoms, an alkenyl group with 2 to 12 carbon atoms, or an aryl group with 6 to 20 carbon atoms);

(B) (B-1) a polyorganosiloxane expressed by the average unit formula:

$(R^c{}_3SiO_{1/2})_p(R^c{}_2SiO_{2/2})_q(R_dSiO_{3/2})_r$ (where $R^c$ may be the same or different, and represents a hydrogen atom, an alkyl group with 1 to 6 carbon atoms, or an aryl group with 6 to 20 carbon atoms, however, in one molecule, at least two $R^c$ are hydrogen atoms; and $R^d$ may be the same or different, and represents an alkyl group with 1 to 6 carbon atoms, or an aryl group with 6 to 20 carbon atoms, and p, q, and r are all numbers that are larger than 0 and that satisfy the equation p+q+r=1);

and/or (B-2) a polyorganosiloxane expressed by the average formula

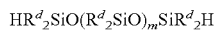

$HR^d{}_2SiO(R^d{}_2SiO)_mSiR^d{}_2H$ (where m is a number larger than 0, and $R^d$ is the same as described above); and (C) a catalyst for a hydrosilylation reaction.

With the polyorganosiloxane (A), in the formula, $R^a$ may be the same or different, and represents an alkyl group with 1 to 6 carbon atoms, or an alkenyl group with 2 to 12 carbon atoms. Examples of the alkyl group of $R^a$ include methyl groups, ethyl groups, propyl groups, butyl groups, pentyl groups, hexyl groups, cyclopentyl groups, cyclohexyl groups, or analogs of alkyl groups. The alkyl group is preferably a methyl group from the perspective of having high reactivity of the polyorganosiloxane (A). Furthermore, examples of the alkenyl group of $R^a$ include vinyl groups, allyl groups, butenyl groups, pentenyl groups, hexenyl groups, and heptenyl groups, and of these, vinyl groups are preferable due to the ease of synthesizing the polyorganosiloxane (A). Incidentally, two or more, preferably three or more, and more preferably four or more of the $R^a$ in one molecule are alkenyl groups. In particular, an alkenyl group at a terminus of a molecular chain can increase the reactivity of the polyorganosiloxane (A), increase the curability of the curable silicone composition, and improve the aggregating properties of the cured silicone particles.

In the formula, $R^b$ may be the same or different, and represents an alkyl group with 1 to 6 carbon atoms, an alkenyl group with 2 to 12 carbon atoms, or an aryl group with 6 to 20 carbon atoms. Examples of the alkyl group of $R^b$ include methyl groups, ethyl groups, propyl groups, butyl groups, pentyl groups, hexyl groups, cyclopentyl groups, cyclohexyl groups, or analogs of alkyl groups. The alkyl group is preferably a methyl group from the perspective of having high reactivity of the polyorganosiloxane (A). Furthermore, examples of the alkenyl group of $R^b$ include vinyl groups, allyl groups, butenyl groups, pentenyl groups, hexenyl groups, and heptenyl groups. Furthermore, examples of the aryl group of $R^a$ include phenyl groups, tolyl groups, xylyl groups, and naphthyl groups.

In the formula, n is 0 or a positive number larger than 0, preferably a number that is 1000 or less, or a number that is 100 or less. This is because making fine particles from the curable silicone composition will be difficult as the value of n increases, or in other words as the viscosity of the polyorganosiloxane (A) increases. The viscosity of the polyorganosiloxane (A) is preferably 1 mPa·s to 1,000,000 mPa·s, 3 mPa·s to 10,000 mPa·s, or 5 mPa·s to 10,000 mPa·s.

Furthermore, the amount of alkenyl groups in the polyorganosiloxane (A) is not limited, but is preferably 0.5 to 30 wt. %, or 1.0 to 27 wt. %. This is because if the amount of alkenyl groups at low viscosity is too high, the cross-linking density of the cured product of the curable silicone composition will be high, and the hardness will become high, and if the hardness is high, the aggregating properties of the cured silicone particle obtained will be improved.

The polyorganosiloxane (B) is a polyorganosiloxane (B-1) expressed by the average unit formula:

$(R^c{}_3SiO_{1/2})_p(R^c{}_2SiO_{2/2})_q(R_dSiO_{3/2})_r$ and/or (B-2) a polyorganosiloxane expressed by the general formula

$HR^d{}_2SiO(R^d{}_2SiO)_mSiR^d{}_2H$.

With the polyorganosiloxane (B-1), in the formula, $R^c$ may be the same or different, and represents a hydrogen atom, an alkyl group with 1 to 6 carbon atoms, or an aryl group with 6 to 20 carbon atoms, however in one molecule, at least two $R^c$ are hydrogen atoms. Examples of the alkyl group of $R^c$ include methyl groups, ethyl groups, propyl groups, butyl groups, pentyl groups, hexyl groups, cyclopentyl groups, cyclohexyl groups, or analogs of alkyl groups. The alkyl group is preferably a methyl group from the perspective of having high reactivity of the polyorganosiloxane (B-1). Furthermore, examples of the aryl group of $R^c$ include phenyl groups, tolyl groups, xylyl groups, and naphthyl groups.

In the formula, $R^d$ may be the same or different, and represents an alkyl group with 1 to 6 carbon atoms or an aryl group with 6 to 20 carbon atoms. Examples of the alkyl group of $R^d$ include methyl groups, ethyl groups, propyl groups, butyl groups, pentyl groups, hexyl groups, cyclopentyl groups, cyclohexyl groups, or analogs of alkyl groups. Furthermore, examples of the aryl group of $R^d$ include phenyl groups, tolyl groups, xylyl groups, and naphthyl groups.

In the formula, p, r, and q are all numbers larger than 0, and are numbers that satisfy the formula p+q+r=1, and preferably are numbers that satisfy the equations 0<p<0.5, 0.33<q<0.97, 0<r<0.34, q>p>r, and p+q+r=1.

Furthermore, the amount of hydrogen atoms bonded to silicon atoms in the polyorganosiloxane (B-1) is not limited, but is preferably 0.5 wt. % or higher, or 0.7 wt. % or higher.

With the polyorganosiloxane (B-2), in the formula, $R^d$ may be the same or different, and represents an alkyl group with 1 to 6 carbon atoms, or an aryl group with 6 to 20 carbon atoms, and examples include the same groups as described above. In particular, $R^d$ is preferably a methyl group because the reactivity will be higher. The polyorganosiloxane (B-2) has a hydrogen atom bonded to a silicone atom on the terminus of the molecular chain because reactivity is higher and curing of the curable silicone composition will be enhanced.

In the formula, m is a number larger than 0, and specifically is a number such that the viscosity of the polyorganosiloxane (B-2) at 25° C. is preferably 10,000 mPa·s or lower. This is because making fine particles from the curable silicone composition will be difficult as the value of m increases, or in other words as the viscosity of the polyorganosiloxane (B-2) increases.

The blending ratio of polyorganosiloxane (A) and polyorganosiloxane (B) is such that the ratio of the number of hydrogen atoms bonded to silicon atoms in the polyorganosiloxane (B) with regard to the number of alkenyl groups in the polyorganosiloxane (A) is preferably 0.5 to 2.0, or 0.7 to 1.2. This is because if the number of hydrogen atoms bonded to silicon atoms exceeds the upper limit of the aforementioned range, there is an increased possibility that hydrogen atoms bonded to silicon atoms will remain in the cured silicone particles. If there are remaining hydrogen atoms bonded to silicon atoms, a change will gradually occur over time, and there is a possibility of having an effect on the dispersibility, aggregating properties, and storage stability.

The hydrosilylation reaction catalyst C is a catalyst that promotes curing of the curable silicone composition, and is preferably a platinum group metal (Group VIII of the periodic table) or a compound thereof. A thermoplastic resin containing platinum and/or a platinum compound, for example fine powdered platinum; chloroplatinic acid or an alcohol solution of chloroplatinic acid; a composite of chloroplatinic acid and an alkenyl siloxane; a composite of platinum and a diketone; silica, alumina, carbon, or a similar platinum metal carrier; or a platinum compound; is preferable. Examples of other platinum group metal catalysts include rhodium, ruthenium, iridium or palladium compounds.

The amount of the hydrosilylation reaction catalyst (C) is preferably such that the amount of platinum metal is 0.5 to 100 ppm, or 1 to 50 ppm, with regard to the total mass of the polyorganosiloxane (A) and the polyorganosiloxane (B).

The curable silicone composition can further contain a polyorganosiloxane (D) expressed by the general formula:

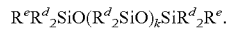

$$R^e R^d_2 SiO(R^d_2 SiO)_k SiR^d_2 R^e.$$

With the polyorganosiloxane (D), in the formula, $R^e$ may be the same or different, and represents an alkenyl group with 2 to 12 carbon atoms. Examples of the alkenyl group of $R^e$ include vinyl groups, allyl groups, butenyl groups, pentenyl groups, hexenyl groups, and heptenyl groups, and of these, vinyl groups are preferable due to the ease of synthesizing the polyorganosiloxane (D).

In the formula, $R^d$ may be the same or different, and represents an alkyl group with 1 to 6 carbon atoms or an aryl group with 6 to 20 carbon atoms, and examples include the same groups as described above.

In the formula, k is a positive number larger than 0, and specifically is a number such that the viscosity of the polyorganosiloxane (D) at 25° C. is preferably 10,000 mPa·s or lower. This is because making fine particles from the curable silicone composition will be difficult as the value of k increases, or in other words as the viscosity of the polyorganosiloxane (D) increases.

The amount of polyorganosiloxane (D) is not limited, but is preferably an amount that is 0 to 95 mass %, or 0 to 80 mass % of the total amount of polyorganosiloxane (A). This is because if the amount of polyorganosiloxane (D) exceeds the upper limit of the aforementioned range, the curing properties of the curable silicone composition will likely be inferior and the effect of improving the aggregating properties of the cured silicone particles will be reduced.

The curable silicone composition forms cured silicone particles by advancement of a curing reaction either by leaving at room temperature, or by heating. The average particle size is 0.1 to 500 μm. This is because if the size is smaller than this, a sufficient cross-linking structure is not achieved, and if larger than this, the blending properties of the particles into the cosmetic material will be lost, and the usage feeling will be inferior.

Next, the method of manufacturing the cured silicone particles of the present invention is described.

The method of manufacturing cured silicone particles of the present invention includes: making fine particles from a mixture of the component (A) and the component (B), adding these fine particles to the component (C) to produce fine particles of a curable silicone composition, and then causing a curing reaction of the composition.

Furthermore, the method of manufacturing other cured silicone particles according to the present invention includes: blending the component (A), the component (B), and the component (C), producing fine particles thereof, and then causing a curing reaction of the composition.

Forming and curing the fine particles of the curable silicone composition can be carried out by a method of spraying the curable silicone composition using a spraying device such as a spray dryer, or the like, and curing, or a method of dispersing the curable silicone composition in water or an aqueous solution of a surfactant, and then curing.

Of these methods for manufacturing cured silicone particles, the method of dispersing the curable silicone composition in water or in an aqueous solution of a surfactant and then curing is particularly preferable from the perspective that spherical cured silicone particles with excellent dispersibility in an aqueous composition can be obtained.

A stirring device such as a homogenizer, colloid mill, or the like, or a mixing device such as an ultrasonic oscillator or the like can be used in order to produce a water-based dispersion of the curable silicone composition. At this time, the curability is preferably controlled by first cooling the curable silicone composition before producing the water-based dispersion of the curable silicone composition.

An aqueous solution of a surfactant is preferably used in order to stabilize the curable silicone composition as particles in the water-based dispersion. The amount of surfactant that is added is an amount that is 0.1 to 20 parts by mass, 0.2 to 10 parts by mass, or 0.2 to 5 parts by mass per 100 parts by mass of the curable silicone composition. The amount of water that is added is an amount that is 40 to 2000 parts by mass, or 40 to 1000 parts by mass per 100 parts by mass of the curable silicone composition. This is because if the amount of water that is added is less than 40 parts by mass per 100 parts by mass of the curable silicone composition, forming a uniform aqueous dispersion of the curable silicone composition will be difficult, but if the amount exceeds 2000 parts by mass, the productivity of the cured silicone particles will be greatly reduced.

The water that is used is preferably ion exchanged water where the metal ions and halogen ions are reduced, preferably where the electric conductivity is 1 µS/cm or less, and particularly preferably 0.5 µS/cm or less, because the aqueous dispersion of the curable silicone composition can be easily stabilized.

If an aqueous dispersion containing fine particles of a mixture of the component (A) and the component (B) is formed, and then the component (C) is added to the fine particle dispersion thereof to produce fine particles of a curable silicone composition, the productivity will be improved, and the fine particles in the aqueous dispersion will not easily aggregate.

Next, the curable silicone composition in the aqueous dispersion can be cured, and a water-based dispersion of the cured silicone particles can be produced by heating or by leaving at room temperature, the water-based dispersion of the curable silicone composition prepared by the aforementioned method.

If the water-based dispersion of the curable silicone composition is heated, the heating temperature is preferably 100° C. or less, particularly 10 to 95° C. Furthermore, examples of the method of heating the water-based dispersion of the curable silicone composition include a method of directly heating the water-based aqueous dispersion, or a method of adding the water-based dispersion to hot water.

Furthermore, the cured silicone particles can be produced by removing the water from the water-based dispersion of the cured silicone particles. Examples of the method of removing water from the water-based dispersion of the cured silicone particles include a method of drying using a vacuum dryer, hot air convection oven, spray dryer, or the like.

The cosmetic material of the present invention is described in detail.

The cosmetic material contains the aforementioned cured silicone particles. Examples of the cosmetic material include: washing cosmetic materials such as soap, body shampoo, facial cleansing cream, and the like; basic cosmetic materials such as lotion, cream, milky lotion, packs, and the like; base makeup cosmetic materials such as face powder, foundation, and the like; lipstick and cheek rouge; eyebrow cosmetic materials such as eye shadow, eyeliner, mascara, and the like; makeup cosmetic materials such as nail polish or the like; cosmetic materials for head hair such as shampoo, hair rinse, hair conditioner, hair growth agent, hair tonic, hair dye, or the like; fragrant cosmetic materials such as perfume, eau de colon, and the like; toothpaste; bathing agents; and specialty cosmetic materials such as depilatory agents, shaving cream, antiperspirants and deodorants, sunscreen, and the like.

Furthermore, examples of the form of the cosmetic preparation include aqueous liquid, oily liquid, emulsion, cream, foam, semisolid, solid and powder. Furthermore, the cosmetic material can be used by spraying.

The content amount of the cured silicone particles in the cosmetic material can be within a range of 0.5 to 99.0 mass %, or within a range of 1.0 to 95 mass % in the cosmetic material. This is because if the content amount of the cured silicone particles exceeds the upper limit of the aforementioned range, the effect of the cosmetic material will be lost, and if the amount is below the lower limit of the aforementioned range, the usage feeling of the cosmetic material and the like will be difficult to improve.

The cosmetic raw material can be made by dispersing the cured silicone particles in an aqueous phase or an oil phase as a medium (aqueous medium or oily medium) containing the cosmetic material components described in the following paragraphs. The aqueous medium can be water such as pure water, ion exchanged water, alkaline ionized water, deep water, wave water, natural water, and the like; or a water-based medium that can be blended with water including lower alcohols such as ethyl alcohol, propyl alcohol, isopropyl alcohol, and the like; and polyhydric alcohols such as glycerin, 1,3-butylene glycol, isoprene glycol, dipropylene glycol, and the like.

Examples of the oily medium (oil) include silicone oils, hydrocarbon oils, higher fatty acids, higher alcohols, ester oils (including fat and oil), ether oils, mineral oils, fluorine oils, and the like. Of these, silicone oils, hydrocarbon oils, and ester oils are more preferable from the perspective of the ease of use. Specific examples include silicone oils such as dimethyl polysiloxane, methyl hydrogen polysiloxane, methyl phenyl polysiloxane, polyether modified organopolysiloxane, fluoroalkyl/polyoxyalkylene co-modified organopolysiloxane, alkyl modified organopolysiloxane, terminal modified organopolysiloxane, fluorine modified organopolysiloxane, amodimethicone, amino-modified organopolysiloxane, acrylic silicone, trimethylsiloxysilicic acid, and the like; hydrocarbon oils such as liquid paraffin, vaseline, squalane, and the like; and ester oils such as; myristyl myristate, hexyl laurate, decyl oleate, isopropyl myristate, hexyldecyl dimethyloctanoate, glyceryl monostearate, diethyl phthalate, ethylene glycol monostearate, octyl oxystearate, isononyl isononanoate, isotridecyl isononanoate, and the like. These oily agents can be a single type, or two or more types can be used. Furthermore, the amount of oily agent with regard to the total amount of an oil in water type emulsion cosmetic material that is used in the present invention is preferably an amount that is 10 to 50 mass %, or 20 to 40 mass % from the perspective of the usage feeling and the storage stability.

The cosmetic material of the present invention can contain components used in normal cosmetic materials within a range that does not hinder the effects of the present invention, such as water, colorants, alcohols, water-soluble polymers, film-forming agents, oil agents, oil-soluble gelling agents, organo-modified clay minerals, surfactants, resins, salts, moisturizing agents, preservatives, antibacterial agents, antioxidants, pH adjusters, chelating agents, refreshing agents, anti-inflammatory agents, skin beautifying components (whitening agents, cell activating agents, skin roughness improving agents, blood circulation promoters, skin astringents, antiseborrheic agents, and the like), vitamins, amino acids, nucleic acids, hormones, clathrate compounds, and the like, bioactive substances, drug activating components, and fragrances, but there is no limitation to these in particular. Note that the amount of these cosmetic material components is within a range of 0.5 to 99.0 mass %, or within a range of 1.0 to 95 mass % of the cosmetic material excluding water. This is because the usage feeling of the cosmetic material will not be favorable if the amount of one component of the cosmetic material exceeds the upper limit of the aforementioned range. Furthermore, this is also because the effect of increasing the sense of use of the cosmetic material will be difficult to achieve if the amount is below the lower limit of the aforementioned range when added. Furthermore, the cosmetic material components and the blending amounts disclosed by Japanese Unexamined Patent Application Publication No. 2015-113303 are incorporated for reference purposes.

The water can be any water that is clean and does not contain components that are harmful to humans, and examples include tap water, pure water, mineral water, and deep-sea water. If the cosmetic material of the present invention is water-based, optional water-soluble additive components can be added to the aqueous phase to the extent that the effects of the present invention are not lost. Furthermore, commonly known pH adjusters, preservatives, antimicrobial agents, and antioxidants can be appropriately added in order to improve the storage stability of the cosmetic material.

Examples of colorants that can be used include colored pigments such as inorganic red pigments such as bengara, iron oxide, iron hydroxide and iron titanate, inorganic brown pigments such as γ-iron oxide, inorganic yellow pigments such as yellow iron oxide and ocher, inorganic black pigments such as black iron oxide and carbon black, inorganic violet pigments such as manganese violet and cobalt violet, inorganic green pigments such as chromium hydroxide, chromium oxide, cobalt oxide and cobalt titanate, inorganic blue pigments such as Prussian blue and ultramarine blue, laked tar colorants such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like, laked natural colorants such as carmine acid, laccaic acid, carthamin, brazilin, crocin, and the like; pearl pigments such as titanium dioxide coated mica, mica titanium, iron oxide treated mica titanium, titanium oxide coated mica, bismuth oxychloride, titanium oxide coated bismuth oxychloride, titanium oxide coated talc, fish scale foil, titanium oxide coated colored mica, and the like; and metal powder such as aluminum, gold, silver, copper, platinum, stainless steel, and the like.

These colorants are preferably water repellent treated. Complexes of these colorants or colorants obtained by surface treatment with general oils, silicone compounds, fluorine compounds, surfactants, or the like can also be used, and one type or two or more types can be used if necessary.

Examples of these water repellent treatments include treating the colorants with various types of water repellent surface treating agents, and examples include methyl hydrogen polysiloxane treatment, silicone resin treatment, silicone rubber treatment, acrylic silicone treatment, chlorinated silicone treatment, and other organosiloxane treatments, zinc stearate treatment and other metal soap treatments, silane coupling agent treatment, alkyl silane treatment, and other silane treatments, perfluoroalkyl silane, perfluoroalkyl phosphate ester treatment, perfluoro polyether treatment, and other fluorine compound treatments, N-lauroyl-L-lysine treatment, other amino acid treatments, squalane treatment, other oily agent treatments, as well as alkyl acrylate treatment, and other acrylic treatments. These treatments can be used in combinations of one or more.

The alcohols can be one or more type selected from lower alcohols, sugar alcohols, and higher alcohols. Specific examples include lower alcohols such as ethanol, isopropanol, and the like; sugar alcohols such as sorbitol, maltose, and the like; and higher alcohols such as lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerin ether (batyl alcohol), and monooleyl glyceryl ether (selachyl alcohol), and the like.

Water soluble polymers are added for the purpose of improving the usage feeling of the cosmetic material, and amphoteric, cationic, anionic, or nonionic polymers, or water-swelling clay minerals that are used in normal cosmetic materials can be used, and one type or two or more types of water soluble polymers can be used in combination. These water soluble polymers have a thickening effect on water-containing components, and are therefore particularly useful when obtaining gel-like water-containing cosmetic materials, water-in-oil emulsion cosmetic materials, or oil-in-water emulsion cosmetic materials.

Examples of amphoteric water-soluble polymers include amphoteric starch, dimethyldiallyl ammonium chloride derivatives (for example, acrylamide/acrylic acid/dimethyldiallyl ammonium chloride copolymer, acrylic acid and dimethyldiallyl ammonium chloride copolymer) and methacrylic acid derivatives (for example, polymethacryloylethyldimethyl betaine, N-methacryloyloxyethyl-N,N-dimethyl ammonium-α-methyl carboxybetaine and alkyl methacrylate copolymer, and the like).

Examples of cationic water-soluble polymers include quaternary nitrogen-modified polysaccharides (for example, cation modified cellulose, cation modified hydroxyethyl cellulose, cation modified guar gum, cation modified locust bean gum, cation modified starch, and the like), dimethyl diallyl ammonium chloride derivatives (for example, dimethyl diallyl ammonium and acrylamide copolymers, polydimethylmethylene piperidinium chloride, and the like), vinylpyrrolidone derivatives (for example, vinylpyrrolidone and dimethylaminoethyl methacrylic acid copolymer salts, vinylpyrrolidone and methacrylamidopropyltrimethyl ammonium chloride copolymer, vinyl pyrrolidone and methylvinyl imidazolium chloride copolymer, and the like), and methacrylic acid derivatives (for example, methacryloyl ethyl dimethyl betaine and methacryloylethyl trimethyl ammonium chloride and 2-hydroxyethyl methacrylate copolymer, methacryloyl ethyl dimethyl betaine and methacryloylethyl trimethyl ammonium chloride and methoxy polyethylene glycol methacrylate copolymer, and the like).

Examples of anionic water-soluble polymers include water-soluble polymers of aliphatic carboxylic acid and metal salts thereof such as polyacrylic acid or alkali metal salts thereof, polymethacrylic acid or alkali metal salts thereof, hyaluronic acid or alkali metal salts thereof, acetylated hyaluronic acid or alkali metal salts thereof, hydrolysate of a methyl vinyl ether and maleic acid anhydride copolymer, and the like; carboxymethylcellulose or alkali metal salts thereof, methyl vinyl ether and maleic acid half ester copolymers, acrylic resin alkanolamine solutions, and carboxyvinyl polymers.

Examples of non-ionic water-soluble polymers include polyvinyl pyrrolidone, highly polymerized polyethylene glycol, vinylpyrrolidone/vinyl acetate copolymer, vinylpyrrolidone/dimethylaminoethyl methacrylate copolymer, vinylcaprolactam/vinylpyrrolidone/dimethylaminoethyl methacrylate copolymer, cellulose or derivatives thereof (for example, methyl cellulose, ethylcellulose, hydroxyethylcellulose, hydroxypropylcellulose, carboxymethylcellulose), keratin and collagen or derivatives thereof, calcium alginate, pullulan, agar, gelatin, tamarind seed polysaccharide, xanthan gum, carrageenan, high methoxyl pectin, low methoxyl pectin, guar gum, pectin, gum arabic, crystalline cellulose, arabinogalactan, karaya gum, tragacanth gum, alginic acid, albumin, casein, curdlan, duran gum, dextran, quince seed gum, tragacanth gum, chitin and chitosan derivatives, starch (rice, maize, potato and wheat, and the like), as well as keratin and collagen or derivatives thereof, and other natural polymer compounds.

Water swelling clay minerals are inorganic water-soluble polymers and are one type of aluminum silicate included in a colloid with a three-layer structure, expressed by the general formula:

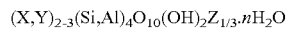

$(X,Y)_{2-3}(Si,Al)_4O_{10}(OH)_2Z_{1/3} \cdot nH_2O$ (where X represents Al, Fe(III), Mn(III), or Cr(III), Y represents Mg, Fe(II), Ni, Zn, or Li, and Z represents K, Na, or Ca).

Specific examples of these inorganic water-soluble polymers include bentonite, montmorillonite, beidellite, nontronite, saponite, hectorite, magnesium aluminum silicate, and silicic anhydride, and these can be either natural or synthetic.

The oily agent can be a solid, semisolid, or liquid. Specific examples include one or more types selected from silicone oil, hydrocarbon oil, ester oil, vegetable fats and oils, animal fats and oils, fatty acids, higher alcohols, triglycerides, artificial sebum, and fluorine oily agents.

Examples of silicone oils include cyclic organopolysiloxane such as hexamethyl cyclotrisiloxane (D3), octamethyl cyclotetrasiloxane (D4), decamethyl cyclopentasiloxane (D5), dodecamethyl cyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl) trimethyl cyclotrisiloxane, 1,3,5,7-tetra(3-methacryloxypropyl) tetramethyl cyclotetrasiloxane, 1,3,5,7-tetra(3-acryloxypropyl) tetramethyl cyclotetrasiloxane, 1,3,5,7-tetra(3-carboxypropyl) tetramethyl cyclotetrasiloxane, 1,3,5,7-tetra(3-vinyloxypropyl) tetramethyl cyclotetrasiloxane, 1,3,5,7-tetra(p-vinylphenyl) tetramethyl cyclotetrasiloxane, 1,3,5,7-tetra[3-(p-vinylphenyl) propyl] tetramethyl cyclotetrasiloxane, 1,3,5,7-tetra(N-acryloyl-N-methyl-3-aminopropyl) tetramethyl cyclotetrasiloxane, and 1,3,5,7-tetra(N,N-bis (lauroyl)-3-aminopropyl) tetramethyl cyclotetrasiloxane, and the like. Examples of straight chain organopolysiloxanes include dimethylpolysiloxane blocked at both molecular chain terminals with trimethylsiloxy groups (dimethyl silicone with a low viscosity of 2 cst or 6 cst to a high viscosity of 1,000,000 cst and the like), organohydrogenpolysiloxane, methylphenylpolysiloxane blocked at both molecular chain terminals with trimethylsiloxy groups, dimethylsiloxane and methylphenylsiloxane copolymer blocked at both molecular chain terminals with trimethylsiloxy groups, diphenylpolysiloxane blocked at both ends of molecular chain terminals with trimethylsiloxy groups, dimethylsiloxane and diphenylsiloxane copolymer blocked at both molecular chain terminals with trimethylsiloxy groups, trimethylpentaphenyltrisiloxane, phenyl(trimethylsiloxy) siloxane, methylalkyl polysiloxane blocked at both molecular chain terminals with trimethylsiloxy groups, trimethylsiloxy group blocked dimethylpolysiloxane and methylalkylsiloxane copolymer blocked at both molecular chain terminals with trimethylsiloxy groups, dimethylsiloxane and methyl(3,3,3-trifluoropropyl) siloxane copolymer blocked at both molecular chain terminals with trimethylsiloxy groups, α,ω-dihydroxypolydimethylsiloxane, α,ω-diethoxypolydimethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, higher alkoxy-modified silicone, and higher fatty acid-modified silicone, and the like.

Examples of hydrocarbon oils include liquid paraffin, light liquid isoparaffin, heavy liquid isoparaffin, Vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene and polypropylene wax, squalane, squalene, pristane, polyisoprene, and the like.

Examples of ester oils include hexyldecyl octanoate, cetyl octanoate, isopropyl myristate, isopropyl palmitate, butyl stearate, hexyl laurate, myristyl myristate, oleyl oleate, decyl oleate, octyl dodecyl myristate, hexyl decyl dimethyl octanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethyl hexanoate, trimethylolpropane tri-2-ethylhexanoate, ditrimethylolpropane triethylhexanoate, ditrimethylolpropane (isostearate/sebacate), trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkyl glycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentyl glycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyl octyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate ester, di(cholesteryl/behenyl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosine, diisostearyl malate, neopentyl glycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethyl pentanediol dineopentanoate, methyl pentanediol dineopentanoate, octyldodecyl neodecanoate, 2-butyl-2-ethyl-1, 3-propanediol dioctanoate, pentaerythrityl tetraoctanoate, pentaerythrityl hydrogenated rosin, pentaerythrityl triethylhexanoate, dipentaerythrityl (hydroxystearate/stearate/rosin acid), polyglyceryl tetraisostearate, polyglyceryl-10 nonaisostearate), polyglyceryl-8 deca(erucate/isostearate/ricinoleate), diglyceryl (hexyldecanoate/sebacate) oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (stearyl/isostearyl/cetyl/stearyl/behenyl) dimer dilinoleate, dimer linoleyl dimer dilinoleate, dimer dilinoleyl diisostearate, dimer linoleyl hydrogenated rosin condensate, hydrogenated castor oil dimer dilinoleate, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl (tricaprylate/caprate/myristate/stearate), hydrogenated rosin triglyceride (hydrogenated ester gum), rosin triglyceride (ester gum), glyceryl behenate eicosanedioic acid, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl macadamia nut oil fatty acid ester, phytosteryl macadamia nut oil fatty acid ester, phytosteryl isostearate, cholesteryl soft lanolin fatty acid ester, cholesteryl hard lanolin fatty acid ester, cholesteryl long chain branched fatty acid ester, cholesteryl long chain α-hydroxy fatty acid ester, octyl dodecyl ricinoleate, octyl dodecyl lanolin fatty acid ester, octyldodecyl erucate, cured castor oil isostearate, ethyl avocado oil fatty acid ester, isopropyl lanolin fatty acid ester, and the like.

Examples of natural plant and animal oils and fats and semisynthetic oils and fats include avocado oil, linseed oil, almond oil, wolfberry wax, perilla oil, olive oil, cacao butter, kapok wax, kaya oil, carnauba wax, liver oil, candelilla wax, beef tallow, beef tallow fat, beef bone fat, cured beef tallow, ginkgo oil, whale wax, hydrogenated oil, wheat germ oil, sesame oil, rice germ oil, rice bran oil, sugarcane wax, sasanqua oil, safflower oil, shea butter, Paulownia oil, cinnamon oil, jojoba wax, olive squalane, shellac wax, turtle oil, soybean oil, tea seed oil, camellia oil, primrose oil, corn oil, pork fat, rapeseed oil, Japanese tung oil, rice bran wax, rice germ oil, horse fat, persic oil, palm oil, palm kernel oil, castor oil, cured castor oil, methyl castor oil fatty acid ester, sunflower oil, grape oil, bayberry wax, jojoba oil, hydrogenated jojoba ester, macadamia nut oil, beeswax, mink oil, cottonseed oil, Japanese wax, Japanese kemal wax, montan wax, coconut oil, cured coconut oil, coconut oil fatty acid glyceride, beef tallow, peanut oil, lanolin, liquid lanolin, reduced lanolin, lanolin alcohol, hard lanolin, lanolin acetate, isopropyl lanolin fatty acid ester, POE lanolin alcohol ether, POE lanolin alcohol acetate, polyethylene glycol lanolin fatty acid ester, POE hydrogenated lanolin alcohol ether, egg yolk oil, and the like. Herein, POE refers to polyoxyethylene.

Examples of higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, and the like.

Specific examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerin ether (batyl alcohol), and monooleyl glyceryl ether (selachyl alcohol), and the like.

Examples of fluorinated oils include perfluoropolyether, perfluorodecalin, perfluorooctane, and the like, and these oily agents can be one type, or two or more types as necessary.

Examples of oil soluble gelling agents include metal soaps such as aluminum stearate, magnesium stearate, zinc myristate, and the like; amino acid derivatives such as N-lauroyl-L-glutamic acid, α,γ-di-n-butylamine, and the like; dextrin fatty acid esters such as dextrin palmitate, dextrin stearate, dextrin 2-ethylhexanoate palmitate, and the like; sucrose fatty acid esters such as sucrose palmitate, sucrose stearate, and the like; fructooligosaccharide fatty acid esters such as inulin stearate, fructo-oligosaccharide 2-ethylhexanoate, and the like; benzylidene derivatives of sorbitol such as monobenzylidene sorbitol, dibenzylidene sorbitol, and the like; organically modified clay minerals such as dimethyl benzyl dodecyl ammonium montmorillonite clay, dimethyl dioctadecyl ammonium montmorillonite clay, and the like.

The surfactant can be one type or two or more types of surfactants used in combination, selected from the group consisting of silicone-based surfactants, anionic surfactants, cationic surfactant, non-ionic surfactant, amphoteric surfactants, and semi-polar surfactants.

Silicone-based surfactants are commonly used for emulsifying and cleaning oils, dispersing powders, and as components for surface treatments, and representative examples include polyglyceryl modified silicone, glyceryl modified silicone, sugar modified silicone, fluorine polyether modified silicone, polyether modified silicone, carboxylic acid modified silicone, sugar modified silicone, linear silicone and polyether block copolymers (polysilicone-13 and the like), long chain alkyl and polyether co-modified silicone, and the like.

Examples of anionic surfactants include saturated or unsaturated fatty acid salts (such as sodium laurate, sodium stearate, sodium oleate, sodium linolenate, and the like), alkyl sulfates, alkylbenzene sulfonic acid (for example hexyl benzenesulfonic acid, octyl benzenesulfonic acid, dodecyl benzenesulfonic acid, and the like), and salts thereof, polyoxyalkylene alkyl ether sulfates, polyoxyalkylene alkenyl ether sulfates, polyoxyethylene alkyl sulfate esters, polyoxyethylene alkyl sulfates, alkyl sulfosuccinate esters, alkyl polyoxyalkylene sulfosuccinate esters, polyoxyalkylene alkylphenyl ether sulfates, alkane sulfonates, octyl trimethyl ammonium hydroxide, dodecyl trimethyl ammonium hydroxide, alkyl sulfonate, polyoxyethylene alkyl phenyl ether sulfate, polyoxyalkylene alkyl ether acetate, alkyl phosphate, polyoxyalkylene alkyl ether phosphate, acyl glutamate, α-acyl sulfonate, alkyl sulfonic acid salt, alkyl allyl sulfonate, α-olefin sulfonate, alkyl naphthalene sulfonate, alkane sulfonate, alkyl or alkenyl sulfate, alkylamide sulfate, alkyl or alkenyl phosphate, alkylamide phosphate, alkyloyl alkyl taurine salt, N-acyl amino acid salt, sulfosuccinate, alkyl ether carboxylate, amide ether carboxylate, α-sulfo fatty acid ester salt, alanine derivatives, glycine derivatives, arginine derivatives, and the like. Examples of salts include alkali metal salts such as sodium salts in the like, alkali earth metal salts such as magnesium salt and the like, alkanolamine salts such as triethanolamine salts and the like, and ammonium salts.

Examples of cationic surfactant include alkyl trimethyl ammonium chloride, stearyl trimethyl ammonium chloride, lauryl trimethyl ammonium chloride, cetyl trimethyl ammonium chloride, beef tallow alkyl trimethyl ammonium chloride, behenyl trimethyl ammonium chloride, stearyl trimethyl ammonium bromide, behenyl trimethyl ammonium bromide, distearyl dimethyl ammonium chloride, distearyl dimethyl ammonium chloride, dicocoyl dimethyl ammonium chloride, dioctyl dimethyl ammonium chloride, di(POE) oleyl methyl ammonium (2 EO) chloride, benzalkonium chloride, alkyl benzalkonium chloride, alkyl dimethyl benzalkonium chloride, benzethonium chloride, stearyldimethylbenzyl ammonium chloride, lanolin derived quaternary ammonium salt, diethyl aminoethylamide stearate, dimethyl aminopropylamide stearate, behenate amidopropyl dimethylhydroxypropyl ammonium chloride, stearoyl colaminoformyl methylpyridinium chloride, cetylpyridinium chloride, tall oil alkyl benzyl hydroxyethyl imidazolinium chloride, benzyl ammonium salt, and the like.

Examples of non-ionic surfactants include polyglyceryl diisostearate, diglyceryl polyhydroxystearate, isostearyl glyceryl ether, polyoxyalkylene ethers, polyoxyalkylene alkyl ethers, polyoxyalkylene fatty acid esters, polyoxyalkylene fatty acid diesters, polyoxyalkylene resin fatty acid esters, polyoxyalkylene (cured) castor oils, polyoxyalkylene alkyl phenols, polyoxyalkylene alkyl phenyl ethers, polyoxyalkylene phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbit fatty acid esters, polyoxyalkylene glycerin fatty acid esters, polyglycerin alkyl ethers, polyglycerin fatty acid esters, sucrose fatty acid esters, fatty acid alkanolamides, alkyl glucosides, polyoxyalkylene fatty acid bisphenyl ethers, polypropylene glycol, diethylene glycol, polyoxyethylene and polyoxypropylene block polymer, alkyl polyoxyethylene and polyoxypropylene block polymer ether, polyoxyethylene and polyoxypropylene block polymer, alkyl polyoxyethylene and polyoxypropylene block polymer ether, fluorine-based surfactants, and the like.

Examples of the amphoteric surfactant include imidazoline type, amidobetaine type, alkylbetaine type, alkylamide betaine type, alkylsulfobetaine type, amidosulfobetaine type, hydroxysulfobetaine type, carbobetaine type, phosphobetaine type, aminocarboxylic acid type, and amidoamino acid type amphoteric surfactants. Specific examples include imidazoline type amphoteric surfactants such as 2-undecyl-N,N,N-(hydroxyethyl carboxy methyl)-2-imidazoline sodium, 2-cocoyl-2-imidazolinium hydroxide-1-carboxyethyloxy-2-sodium salt and the like; alkylbetaine type amphoteric surfactants such as lauryldimethylaminoacetic acid betaine, myristyl betaine, and the like; amidobetaine type amphoteric surfactants such as coconut oil fatty acid amidopropyldimethylaminoacetic acid betaine, palm kernel oil fatty acid amidopropyldimethylaminoacetic acid betaine, beef tallow fatty acid amidopropyldimethylaminoacetic acid betaine, cured tallow fatty acid amidopropyldimethylaminoacetic acid betaine, laurate amidopropyldimethylaminoacetic acid betaine, myristate amidopropyl dimethylaminoacetic acid betaine, palmitate amidopropyldimethylaminoacetic acid betaine, stearate amidopropyldimethylaminoacetic acid betaine, and oleate amidopropyldimethylaminoacetic acid betaine, and the like; alkylsulfobetaine type amphoteric surfactants such as coconut oil fatty acid dimethylsulfopropyl betaine and the like; alkyl hydroxysulfobetaine type amphoteric surfactants such as lauryl dimethyl amino sulfobetaine, and the like; phosphobetaine type amphoteric surfactants such as lauryl hydroxyphosphobetaine, and the like; and amido amino acid type amphoteric surfactants such as N-lauroyl-N'-hydroxyethyl-N'-carboxymethyl ethylenediamine sodium, N-oleyl-N'-hydroxyethyl-N'-carboxymethyl ethylenediamine sodium, N-cocoyl-N'-hydroxyethyl-carboxymethyl ethylenediamine sodium, N-lauroyl-N'-hydroxyethyl-N'-carboxymethyl ethylenediamine potassium, N-oleyl-N'-hydroxyethyl-N'-carboxymethyl ethylenediamine potassium, N-lauroyl-N'-carboxymethyl ethylenediamine sodium, N-oleyl-N-hydroxyethyl-N'-carboxymethyl ethylenediamine sodium, N-cocoyl-N-hydroxyethyl-N'-carboxymethyl ethylenediamine sodium, N-lauroyl-N-hydroxyethyl-N', N'-dicarboxymethyl ethylenediamine monosodium, N-oleyl-N-hydroxyethyl-N',N'-dicarboxymethyl ethylenediamine monosodium, N-cocoyl-N-hydroxyethyl-N',N'-dicarboxymethyl ethylenediamine monosodium, N-lauroyl-N-hydroxyethyl-N',N'-dicarboxymethyl ethylenediamine disodium, N-oleoyl-N-hydroxyethyl-N',N'-dicarboxymethylethylenediamine disodium, N-cocoyl-N-hydroxyethyl-N', N'-dicarboxymethyl ethylenediamine disodium, and the like.

Semi-polar surfactants include alkylamine oxide type surfactants, alkyl amine oxide, alkyl amidoamine oxide, alkyl hydroxyamine oxide, and the like, but alkyldimethyl amine oxides with 10 to 18 carbon atoms and alkoxyethyl dihydroxyethyl amine oxides with 8 to 18 carbon atoms are preferably used. Specific examples include dodecyl dimethyl amine oxide, dimethyl octyl amine oxide, diethyl decyl amine oxide, bis-(2-hydroxyethyl) dodecyl amine oxide, dipropyl tetradecyl amine oxide, methylethyl hexadecyl amine oxide, dodecyl amidopropyl dimethyl amine oxide, cetyl dimethyl amine oxide, stearyl dimethyl amine oxide, tallow dimethyl amine oxide, dimethyl-2-hydroxyoctadecyl amine oxide, lauryl dimethyl amine oxide, myristyl dimethyl amine oxide, stearyl dimethyl amine oxide, isostearyl dimethyl amine oxide, coconut fatty acid alkyl dimethyl amine oxide, caprylic acid amidopropyldimethylamine oxide, capric acid amidopropyldimethylamine oxide, lauric acid amidopropyldimethylamine oxide, myristic acid amidopropyldimethylamine oxide, palmitic acid amidopropyldimethylamine oxide, stearic acid amidopropyldimethylamine oxide, isostearic acid amidopropyldimethylamine oxide, oleic acid amidopropyldimethylamine oxide, ricinoleic acid amidopropyldimethylamine oxide, 12-hydroxystearic acid amidopropyldimethylamine oxide, coconut fatty acid amidopropyldimethylamine oxide, palm kernel oil fatty acid amidopropyldimethylamine oxide, castor oil fatty acid amidopropyldimethylamine oxide, lauric acid amidoethyldimethylamine oxide myristic acid amidoethyldimethylamine oxide, coconut fatty acid amidoethyldimethylamine oxide, lauric acid amidoethyldiethylamine oxide, myristic acid amidoethyldiethylamine oxide, coconut fatty acid amidoethyldiethylamine oxide, lauric acid amidoethyldihydroxyethylamine oxide, myristic acid amidoethyl dihydroxyethylamine oxide, coconut fatty acid amide ethyl dihydroxyethylamine oxide, and the like.

The salt can be an inorganic salt, organic salt, amine salt, or amino acid salt. Examples of inorganic salts include sodium salts, potassium salts, magnesium salts, calcium salts, aluminum salts, zirconium salts, zinc salts, and the like of inorganic acids such as hydrochloric acid, sulfuric acid, carbonic acid, nitric acid, and the like; examples of organic salts include salts of organic acids such as acetic acid, dehydroacetic acid, citric acid, malic acid, succinic acid, ascorbic acid, stearic acid, and the like; and examples of amine salts and amino acid salts include salts of amines such as triethanolamine and the like, and salts of amino acids such as glutamic acid and the like. Furthermore, in addition, salts of hyaluronic acid, chondroitin sulfate, and the like, aluminum zirconium glycine complex and the like, and neutral salts of acid and bases that are used in cosmetic formulations, and the like, can also be used.

Examples of moisture retaining agents include polyhydric alcohols such as glycerin, sorbitol, propylene glycol, dipropylene glycol, 1,3-butylene glycol, glucose, xylitol, maltitol, polyethylene glycol, and the like; as well as hyaluronic acid, chondroitin sulfate, pyrrolidone carboxylate, polyoxyethylene methyl glucoside, polyoxypropylene methyl glucoside, PEG/PPG dimethyl ether, and the like.

Examples of preservatives include alkyl p-hydroxybenzoate ester, benzoic acid, sodium benzoate, sorbic acid, potassium sorbate, phenoxyethanol and the like. Examples of antimicrobial agents include benzoic acid, salicylic acid, carbolic acid, sorbic acid, alkyl paraoxybenzoate, parachloromethacresol, hexachlorophene, benzalkonium chloride, chlorhexidine chloride, trichlorocarbanilide, triclosan, photosensitizers, phenoxyethanol, and the like.

Examples of antioxidants include tocopherol, butylhydroxyanisole, dibutylhydroxytoluene, phytic acid, and the like.

Examples of pH adjusters include lactic acid, citric acid, glycolic acid, succinic acid, tartaric acid, dl-malic acid, potassium carbonate, sodium bicarbonate, ammonium bicarbonate, and the like.

Examples of chelating agents include alanine, sodium edetate, sodium polyphosphate, sodium metaphosphate, phosphoric acid, and the like.

Examples of refreshing agents include L-menthol, camphor and the like. Examples of anti-inflammatory agents include allantoin, glycyrrhetinic acid, glycyrrhizic acid, tranexamic acid, azulene, and the like.

Examples of skin beautifying components include whitening agents such as placenta extract, albutin, glutathione, yukinoshita extract, and the like; cell activators such as royal jelly, and the like; rough skin improving agents; blood circulation promoters such as nonanoic acid vanillylamide, benzyl nicotinate ester, β-butoxyethyl nicotinate ester, capsaicin, zigerone, cantharis tincture, ichthammol, caffeine, tannic acid, α-borneol, tocopherol nicotinate, inositol hexanicotinate, cyclandelate, cinnarizine, tolazoline, acetylcholine, verapamil, cepharanthine, γ-oryzanol, and the like; skin astringents such as zinc oxide, tannic acid, and the like; anti-seborrhoeic agents such as sulfur, thiantrol, and the like. Examples of vitamins include A type vitamins such as vitamin A oil, retinol, retinol acetate, retinol palmitate, and the like; B type vitamins such as B2 vitamins such as riboflavin, riboflavin butyrate, flavin adenine nucleotide, and the like, B6 vitamins such as pyridoxine hydrochloride, pyridoxine dioctanoate, pyridoxine tripalmitate, and the like, vitamin B12 and derivatives thereof, vitamin B15 and derivatives thereof; C type vitamins such as L-ascorbic acid, L-ascorbate dipalmitate, sodium L-ascorbate-2-sulfate, dipotassium L-ascorbyl phosphate diester, and the like; D type vitamins such as ergocalciferol, cholecalciferol, and the like; E type vitamins such as α-tocopherol, β-tocopherol, γ-tocopherol, dl-α-tocopherol acetate, dl-α-tocopherol nicotinate, dl-α-tocopherol succinate, and the like; vitamin H; vitamin P; nicotinic acids such as nicotinic acid, benzyl nicotinate, and the like; pantothenic acid such as calcium pantothenate, D-pantothenyl alcohol, pantothenyl ethyl ether, acetyl pantothenyl ethyl ether, and the like.

Examples of amino acids include glycine, valine, leucine, isoleucine, serine, threonine, phenylalanine, arginine, lysine, aspartic acid, glutamic acid, cystine, cysteine, methionine, tryptophan, and the like, and/or salts thereof.

Examples of nucleic acids include deoxyribonucleic acid and the like. Examples of hormones include estradiol, ethenyl estradiol, and the like.

Physiologically active components are substances that provide some form of physiological activity to the skin or hair when applied to the skin or hair, and these components are lipophilic.

Examples include anti-inflammatory agents, anti-aging agents, tightening agents, hair growth agents, hair thickening agents, moisturizing agents, blood circulation promoting agents, drying agents, warming agents, vitamins, wound healing accelerators, irritation relieving agents, analgesic agents, cell activators, enzyme components, and the like. Similarly, natural plant extract components, seaweed extract components, and/or raw drug components can be preferably added.

Pharmaceutically active components are substances that have a disease therapeutic effect, and examples include proteins, peptides, and low molecular weight compounds.

Perfumes are not particularly limited so long as they are lipophilic perfumes, and include perfumes extracted from flowers, seeds, leaves, roots, or the like of various plants, perfumes extracted from seaweeds, perfumes extracted from various parts or secretions of animals (for example, musk, spermaceti oil), and artificially synthesized fragrances (for example, menthol, musk, acetate esters, vanilla). The perfume is added in order to provide fragrance and aroma to the cosmetic material. Colorants include oil soluble dyes, body pigments, inorganic pigments, organic pigments, lipophilic fluorescent whiteners, and the like.

The cosmetic material of the present invention can easily be manufactured by simply uniformly mixing the aforementioned raw materials of the cosmetic material of the present invention and other cosmetic raw materials. The mixing means can be any type of mixing device or kneading device that is used for manufacturing normal cosmetic materials. Examples of these devices include homomixers, paddle mixers, Henschel mixers, homodispersers, colloid mixers, propeller stirrers, homogenizers, inline type continuous emulsifying machines, ultrasonic emulsifying machines, vacuum type kneading machines, and the like.

EXAMPLES

The silicone powder of the present invention and the method for manufacturing will be described in detail using examples and comparative examples. However, the present invention is not limited to these examples. Viscosity in the examples refers to the value at 25° C. Furthermore, the properties of the cured silicone particles were measured as follows.

<JIS a Hardness of Cured Silicone Particles>

The curable silicone composition which is a raw material of the cured silicone particles was heated to 150° C. for 1 hour using a heating oven and cured to a sheet shape. The hardness was measured using a JIS A hardness meter as specified by JIS K6301.

<Average Particle Size of Primary Particles>

The emulsion prior to adding the platinum catalyst was measured using a laser diffraction type particle size distribution analyzer (LS-230 by Beckman Coulter), and the median diameter (particle size corresponding to 50% cumulative distribution, 50% particle size) was used as the average particle size.

<Powder Particle Size>

Using ethanol as a dispersion medium, the particle size of the cured silicone particles was measured with a laser diffraction type particle size distribution analyzer (LA-750 by Horiba, Ltd.), and values for the median diameter of the cured silicone particles in ethanol (particle size corresponding to 50% cumulative distribution, D50, am), 90% particle size (particle size corresponding to 90% cumulative distribution, D90, am), and the arithmetic dispersity (indicating the degree of dispersion of the particle size distribution, SD, m2) were obtained. For the measurement sample, 1 g of cured silicone particles and 100 mL of ethanol were dispersed in a 300 mL cup using a stirring device or an ultrasonic vibrator.

The components used in the examples and comparative examples are shown below.

In the following formulas, Vi represents a vinyl group, and Me represents a methyl group.

Compound 1-1

Polyorganosiloxane expressed by the average formula:

[ViMe$_2$SiO(Me$_2$SiO)$_n$]$_4$Si (n is a number that averages approximately 10.0 to 11.0, the content amount of vinyl groups is 3.15 mass %, and the viscosity is 35 mPa·s)

Compound 1-2

Polyorganosiloxane expressed by the average formula:

[ViMe$_2$SiO(Me$_2$SiO)$_n$]$_4$Si (n is a number that averages approximately 30.0, the content amount of vinyl groups is 1.16 mass %, and the viscosity is 120 mPa·s)

Compound 1-3

Polyorganosiloxane expressed by the formula:

ViMe$_2$SiO(Me$_2$SiO)$_{165}$SiMe$_2$Vi (the content amount of vinyl groups is 0.457 mass %, and the viscosity is 450 mPa·s)

Compound 1-4

Polyorganosiloxane expressed by the average formula:

[ViMe$_2$SiO(Me$_2$SiO)$_n$]4Si (n is a number that averages approximately 0.46, and the viscosity is 20 mPa·s)

Compound 1-5

Polyorganosiloxane expressed by the formula:

ViMe$_2$SiO(Me$_2$SiO)$_{130}$(ViMeSiO)$_2$SiMe$_2$Vi (the content amount of vinyl groups is 1.08 mass %, and the viscosity is 370 mPa·s)

Compound 2-1

Polyorganosiloxane expressed by the formula:

HMe$_2$SiO(Me$_2$SiO)$_{14}$SiMe$_2$H (the content amount of hydrogen atoms bonded to a silicon atom is 0.15 mass %, and the viscosity is 15 mPa·s)

Compound 2-2

Polyorganosiloxane expressed by the average unit formula:

(Me$_3$SiO$_{1/2}$)$_{0.10}$(Me$_2$SiO$_{2/2}$)$_{0.33}$(HMeSiO$_{2/2}$)$_{0.52}$(MeSiO$_{3/2}$)$_{0.05}$ (the content amount of hydrogen atoms bonded to a silicon atom is 0.825 mass %, and the viscosity is 15 mPa·s)

Compound 2-3

Polyorganosiloxane expressed by the average formula:

Me$_3$SiO(Me$_2$SiO)$_{33.7}$(HMeSiO)$_{11.5}$SiMe$_3$ (the content amount of hydrogen atoms bonded to a silicon atom is 0.44 mass %, and the viscosity is 50 mPa·s)

Compound 2-4

Polyorganosiloxane expressed by the average formula:

Me$_3$SiO(Me$_2$SiO)$_{51.3}$(HMeSiO)$_{6.3}$SiMe$_3$ (the content amount of hydrogen atoms bonded to a silicon atom is 0.146 mass %, and the viscosity is 57 mPa·s)

Example 1

An amount of 51.7 parts by mass of the polyorganosiloxane of [compound 1-1] and the polyorganosiloxane of [compound 2-1] (of an amount such that the ratio of silicon atom-bonded hydrogen atoms in the present component to the vinyl groups in the polyorganosiloxane was 1.0) were uniformly mixed at room temperature to prepare an addition reaction curable silicone composition. Next, the composition was dispersed in a 25° C. aqueous solution containing 0.4 parts by mass of polyoxyethylene alkyl (C12-14) ether and 50 parts by mass of pure water, and then uniformly emulsified using a colloid mill, after which dilution was performed by adding 350 parts by mass of pure water to produce an emulsion. Next, an isopropyl alcohol solution of chloroplatinic acid (of an amount such that the platinum metal was 10 ppm by mass in the composition) and polyoxyethylene alkyl (C12-14) ether were added and stirred into the emulsion using pure water as the aqueous dispersion, and then the emulsion was left to stand for 3 hours at 50° C. to produce a uniform water-based suspension of silicone rubber particles. Next, the water-based suspension was dried using a small spray dryer (produced by Ashizawa) to obtain cured silicone particles.

Example 2

An amount of 94.9 parts by mass of the polyorganosiloxane of [compound 1-2] and the polyorganosiloxane of [compound 2-2] (of an amount such that the ratio of silicon atom-bonded hydrogen atoms in the present component to vinyl groups in the polyorganosiloxane was 1.0) were uniformly mixed at room temperature to prepare an addition reaction curable silicone composition. Next, this composition was used similar to Example 1 to obtain cured silicone particles.

Example 3

An amount of 45.0 parts by mass of the polyorganosiloxane of [compound 1-1], 45.0 parts by mass of the polyorganosiloxane of [compound 1-3] and the polyorganosiloxane according to [compound 2-2] (of an amount such that the ratio of silicon atom-bonded hydrogen atoms in the present component to vinyl groups in the polyorganosiloxane was 1.0) were uniformly mixed at room temperature to prepare an addition reaction curable silicone composition. Next, this composition was used similar to Example 1 to obtain cured silicone particles.

Example 4

An amount of 14.3 parts by mass of the polyorganosiloxane of [compound 1-4], and the polyorganosiloxane of [compound 2-1] (of an amount such that the ratio of silicon atom-bonded hydrogen atoms in the present component to vinyl groups in the polyorganosiloxane was 1.0) were uniformly mixed at room temperature to prepare an addition reaction curable silicone composition. Next, this composition was used similar to Example 1 to obtain cured silicone particles.

Example 5

An amount of 87.6 parts by mass of the polyorganosiloxane of [compound 1-1] and the polyorganosiloxane of [compound 2-2] (of an amount such that the ratio of silicon atom-bonded hydrogen atoms in the present component to vinyl groups in the polyorganosiloxane was 1.0) were uniformly mixed at room temperature to prepare an addition reaction curable silicone composition. Next, this composition was used similar to Example 1 to obtain cured silicone particles.

Example 6

An amount of 45.0 parts by mass of the polyorganosiloxane of [compound 1-1], 45.0 parts by mass of the polyorganosiloxane of [compound 1-3] and the polyorganosiloxane of [compound 2-2] (of an amount such that the ratio of silicon atom-bonded hydrogen atoms in the present component to vinyl groups in the polyorganosiloxane was 1.0) were uniformly mixed at room temperature to prepare an addition reaction curable silicone composition. The composition was dispersed in an aqueous solution containing 0.1 parts by mass of polyoxyethylene alkyl (C12-14) ether and 50 parts by mass of pure water at 25° C., and then this composition was used similar to Example 1 to obtain cured silicone particles.

Comparative Example 1

An amount of 90.8 parts by mass of the polyorganosiloxane of [compound 1-2] and the polyorganosiloxane of [compound 2-3] (of an amount such that the ratio of silicon atom-bonded hydrogen atoms in the present component to vinyl groups in the polyorganosiloxane was 1.0) were uniformly mixed at room temperature to prepare an addition reaction curable silicone composition. Next, this composition was used similar to Example 1 to obtain cured silicone particles.

Comparative Example 2

An amount of 78.5 parts by mass of the polyorganosiloxane of [compound 1-5] and the polyorganosiloxane of [compound 2-4] (of an amount such that the ratio of silicon atom-bonded hydrogen atoms in the present component to vinyl groups in the polyorganosiloxane was 1.0) were uniformly mixed at room temperature to prepare an addition reaction curable silicone composition. Next, this composition was used similar to Example 1 to obtain cured silicone particles.

Comparative Example 3

An amount of 97.9 parts by mass of the polyorganosiloxane of [compound 1-3] and the polyorganosiloxane of [compound 2-2] (of an amount such that the ratio of silicon atom-bonded hydrogen atoms in the present component to vinyl groups in the polyorganosiloxane was 1.0) were uniformly mixed at room temperature to prepare an addition reaction curable silicone composition. Next, this composition was used similar to Example 1 to obtain cured silicone particles.

The properties of the cured silicone particles provided by Examples 1 to 6 and Comparative Examples 1 to 3 are shown in Table 1.

TABLE 1

| | | Average particle size of primary particles (μm) | Dispersed particle size in ethanol | | | Median size (μm)/ average particle size of primary particles (μm) |
| --- | --- | --- | --- | --- | --- | --- |
| | JIS-A hardness | | Median diameter (μm) | 90% particle diameter (μm) | Dispersibility (SD, μm$^2$) | |
| Example 1 | 30 | 6.1 | — | — | — | — |
| Example 2 | 49 | 7.1 | 10 | 23 | 86 | 1.4 |
| Example 3 | 61 | 7.2 | 7 | 11 | 8 | 1.0 |
| Example 4 | 66 | 6.6 | 9 | 17 | 23 | 1.4 |
| Example 5 | 72 | 6.8 | 5 | 8 | 3 | 0.8 |
| Example 6 | 61 | 12.7 | 11 | 18 | 27 | 0.9 |
| Comparative Example 1 | 44 | 6.9 | 41 | 74 | 645 | 5.9 |
| Comparative Example 2 | 44 | 7.2 | 18 | 43 | 398 | 2.5 |
| Comparative Example 3 | 15 | 7.3 | 20 | 39 | 182 | 2.8 |

Examples 7 to 9, Comparative Example 4

The viscosity of a mixture of the cured silicone particles and decamethylcyclopentasiloxane is shown in Table 2.

<Measurement Method for Liquid Mixture Viscosity>

An amount of 6 g of the cured silicone particles and 58 g of decamethylcyclopentasiloxane were weighed in a 300 mL cup, and stirring was performed for 2 minutes at 4000 rpm using a disperser. Next, the value obtained after stirring for 1 minute at 60 rpm using a rotor No. 2 of a BM type rotational viscometer (manufactured by TOKI SANGYO Co., Ltd.) was used as the viscosity.

TABLE 2

| | Mixed cured silicone particles | Viscosity of decamethylcyclopentasiloxane mixture solution (mPa·s) |
| --- | --- | --- |
| Example 7 | Example 1 | 30 |
| Example 8 | Example 2 | 10 |
| Example 9 | Example 4 | 8 |
| Comparative Example 4 | Comparative Example 3 | 56 |

Example 10, Comparative Example 5

The skin cream shown in Table-3 was prepared using the cured silicone particles from Example 3 and Comparative Example 1, and a 3-step evaluation was performed by a ten member expert evaluation panel in accordance with the following standards by evaluating whether or not the lotion was compatible with the skin after application, and a judgment was made based on the average of these evaluations. Example 10 provided better skin compatibility than Comparative Example 5.

<Evaluation>

5 points: Absorbed extremely well into the skin 3 points: Normal 1 point: Did not absorb well into the skin <Evaluation>

○: Average of 4.0 or more points

Δ: Average of 2.0 or more and less than 4.0 points x: Average of less than 2.0 points

TABLE 3

| | Component | Example 10 | Comparative Example 5 |
|---|---|---|---|
| | Oil phase | | |
| 1 | Lauryl PEG/PPG-18/18 dimethicone*[1] | 2 | 2 |
| 2 | Bis(hydroxyethoxypropyl) dimethicone*[2] | 2 | 2 |
| 3 | Isopropyl palmitate*[3] | 1 | 1 |
| 4 | Cyclopentasiloxane*[4] | 6.5 | 6.5 |
| 5 | Mineral oil*[5] | 10 | 10 |
| 6 | Vaseline | 1.5 | 1.5 |
| 7 | Silicone cross-linked body of Example 3 | 5 | |
| 7 | Silicone cross-linked body of Comparative Example 1 | | 5 |
| | Water phase | | |
| 8 | Glycerin | 5 | 5 |
| 9 | Sodium chloride | 1 | 1 |
| 10 | Water | 66 | 66 |

TABLE 3-continued

| Component | Example 10 | Comparative Example 5 |
|---|---|---|
| Skin compatibility feel | ○ | X |

*[1] 5200 Formulation Aid produced by Dow Corning Toray
*[2] 5562 Carbinol Fluid produced by Dow Corning Toray
*[3] Excepar1 IPM produced by Kao Corporation
*[4] SH245 produced by Dow Corning Toray
*[5] Hicall K-230 produced by Kaneda Corp.

Examples 11, 12, Comparative Example 6

The body powder shown in Table 4 was prepared using the cured silicone particles from Example 3, Example 5, and Comparative Example 1, and a 3-step evaluation was performed by a 10 member expert panel according to the following standards by evaluating the ease of spreading when applying to the skin, and whether or not the skin was smooth after application, and a judgment was made based on the average of these evaluations. Example 11 and Example 12 were confirmed to provide better ease of spread and smooth feel as compared to Comparative Example 6.

<Evaluation of Ease of Spreading>

5 points: Can easily be spread 3 points: Normal 1 point: Difficult to spread

<Evaluation>

○: Average of 4.0 or more points

Δ: Average of 2.0 or more and less than 4.0 points x: Average of less than 2.0 points <Evaluation of Smoothness>

5 points: Skin feels smooth after application 3 points: Normal 1 point: Skin does not feel smooth after application <Evaluation>

○: Average of 4.0 or more points

Δ: Average of 2.0 or more and less than 4.0 points x: Average of less than 2.0 points

TABLE 4

| | Component | Example 11 | Example 12 | Comparative Example 6 |
|---|---|---|---|---|
| 1 | Titanium oxide | 13.43 | 13.43 | 13.43 |
| 2 | Yellow iron oxide*[1] | 2.43 | 2.43 | 2.43 |
| 3 | Red iron oxide*[2] | 0.97 | 0.97 | 0.97 |
| 4 | Black iron oxide*[3] | 0.17 | 0.17 | 0.17 |
| 5 | Silicone cross-linked body of Example 3 | 51 | | |
| 5 | Silicone cross-linked body of Example 5 | | 51 | |
| 5 | Silicone cross-linked body of Example 1 | | | 51 |
| 6 | Perfume | 2.5 | 2.5 | 2.5 |
| 7 | Cyclopentasiloxane*[4] | 27.5 | 27.5 | 27.5 |
| 8 | (Ca/Na) borosilicate, titanium oxide*[5] | 2 | 2 | 2 |
| Feel evaluation | Ease of spreading | ○ | ○ | X |
| | Sense of smoothness | ○ | ○ | Δ |

*[1] SA-IOY-8 produced by Miyoshi Kasei Inc.
*[2] SA-IOR-8 produced by Miyoshi Kasei Inc.
*[3] SA-IOB-8 produced by Miyoshi Kasei Inc.
*[4] SH245 produced by Dow Corning Toray
*[5] Pinpoints of Pearl produced by BASF A formulation example of a cosmetic material of the present invention made by adding the cured silicone particles of the present invention is shown below. However, the present invention is not restricted to these examples.

Formulation Example 1: W/O BB Cream (Ingredients)
Phase A
1) Lauryl PEG/PPG-18/18 dimethicone (Note 1): 4 parts by mass
2) Caprylylmethicone (Note 2): 14 parts by mass
3) Ethylhexyl methoxycinnamate (Note 3): 7.5 parts by mass
4) Hexyl diethylaminohydroxybenzoylbenzoate (Note 4): 1.5 parts by mass
5) Ethylhexyl salicylate: 2.5 parts by mass
6) Trimethylsiloxysilic acid, polypropylsilsesquioxane (Note 5): 2 parts by mass
7) Silicone crosslinked body of the examples: 3 parts by mass
8) Tocopherol acetate: 0.5 parts by mass
Phase B
9) Sodium ascorbyl phosphate: 0.5 parts by mass
10) Glycerin: 8 parts by mass
11) Sodium chloride: 0.7 parts by mass
12) Pure water: 39.8 parts by mass
Phase C
13) Titanium oxide: 5.6 parts by mass
14) Yellow iron oxide (Note 6): 0.25 parts by mass
15) Red iron oxide (Note 7): 0.1 parts by mass
16) Black iron oxide (Note 8): 0.05 parts by mass
17) Phenyl trimethicone (Note 9): 9.2 parts by mass
18) Zinc oxide (Note 10): 0.8 parts by mass
Note 1: 5200 Formulation Aid manufactured by Dow Corning Toray
Note 2: FZ-3196 manufactured by Dow Corning Toray
Note 3: Uvinul MC80N manufactured by BASF
Note 4: Uvinal A Plus Granular manufactured by BASF
Note 5: MQ-1640 Flake Resin manufactured by Dow Corning Toray
Note 6: SA-IOY-8 manufactured by Miyoshi Kasei
Note 7: SA-IOR-8 manufactured by Miyoshi Kasei
Note 8: SA-IOB-8 manufactured by Miyoshi Kasei
Note 9: SH556 manufactured by Dow Corning Toray
Note 10: Z-Cote manufactured by BASF The BB cream of Formulation Example 1 was adjusted using the following procedure.
1. Mix ingredients 1 to 8.
2. Mix ingredients 9 to 12.
3. Mix ingredients 13 to 18.
4. Mix phase A obtained from step 1 and phase C obtained from step 3.
5. Perform emulsification by slowly adding phase B obtained from step 2 while stirring the mixture obtained from step 4.

Formulation Example 2: Sunblocking Non-Aqueous Lotion (Ingredients)
(1) Zinc oxide (Note 1): 6 parts by mass
(2) Ethylhexyl methoxycinnamate (Note 2): 7.5 parts by mass
(3) Dimethicone, dimethicone cross polymer (Note 3): 24 parts by mass
(4) Cyclopentasiloxane (Note 4): 60.5 parts by mass
(5) Silicone crosslinked body from the example: 2 parts by mass
Note 1: MZ-303S manufactured by TAYCA
Note 2: Uvinul MC80N manufactured by BASF
Note 3: 9041 Silicone Elastomer Blend manufactured by Dow Corning Toray
Note 4: SH245 manufactured by Dow Corning Toray The sunblocking non-aqueous lotion in Formulation Example 2 was prepared according to the following procedure.
1. Stir the ingredient 4 and the ingredient 5 until uniform.
2. Add the product from step 1 to the ingredient 3 and stir until uniform.
3. Mix the ingredient 1 and the ingredient 2.
4. Stir together the products from steps 2 and 3 until uniform.

Formulation Example 3: O/W Anti-Aging Cream (Ingredients)
Phase A
(1) Pure water: remainder
(2) Methyl methacrylate crosspolymer (Note 1): 5 parts by mass
Phase B
(3) Cyclopentasiloxane, cyclohexasiloxane (Note 2): 35 parts by mass
(4) Silicone crosslinked body from example: 5 parts by mass
(5) (Hydroxyethyl acrylate/acryloyl dimethyl taurine Na) copolymer, squalane, polysorbate 80, water, sorbitan oleate (Note 3): 0.7 parts by mass
(6) (Hydroxyethyl acrylate/acryloyl dimethyl taurine Na) copolymer, isohexadecane, polysorbate 60, water, sorbitan isostearate (Note 4): 0.7 parts by mass
Phase C
(7) Dimethicone: 5 parts by mass
(8) Dipalmitoyl hydroxyproline (Note 5): 0.5 parts by mass
Phase D
(9) Wine extract (Note 6): 0.01 parts by mass
(10) Perfume: 0.2 parts by mass
Phase E
(11) Phenoxyethanol: 0.9 parts by mass
Note 1: Micropearl M305 manufactured by SEPPIC S.A. Co., Ltd.
Note 2: DC 345 manufactured by Dow Corning Toray
Note 3: Simulgel EG manufactured by SEPPIC S.A. Co., Ltd.
Note 4: Simulgel NS manufactured by SEPPIC S. A. Co., Ltd.
Note 5: Sepilift DPHP manufactured by SEPPIC S.A. Co., Ltd.
Note 6: Sepivinol R manufactured by SEPPIC S.A. Co., Ltd.

The O/W anti-aging cream of Formulation Example 3 was prepared according to the following procedures.
1. Disperse the ingredient 2 in the ingredient 1.
2. Disperse the ingredient 4 in the ingredient 3.
3. Add the ingredient 5 and the ingredient 6 to the product from step 2 and mix.
4. Dissolve the ingredient 8 in the ingredient 7.
5. While stirring the product from step 1, perform emulsification by adding the products from steps 3 and 4 as well as phase D.

6. While stirring the product from step 1, perform emulsification by adding the products from steps 3 and 4 as well as phase D.

Formulation Example 4: O/W Wrinkle Care Cream (Ingredients)
Phase A
1) Cyclopentasiloxane (Note 1): 11 parts by mass
2) Silicone crosslinking body from the example: 10 parts by mass
3) Lauryl PEG/PPG-18/18 dimethicone (Note 2): 0.5 parts by mass
4) PEG-12 dimethicone (Note 3): 4 parts by mass
Phase B
5) Pure water: 72.5 parts by mass
Phase C
6) Polyacrylamide, water, (C13, 14) isoparaffin, Laureth-7 (Note 4): 2 parts by mass
Note 1: SH 245 manufactured by Dow Corning Toray
Note 2: 5200 Formulation Aid manufactured by Dow Corning Toray
Note 3: OFX-5329 manufactured by Dow Corning Toray
Note 4: Simulgel NS manufactured by SEPPIC S. A. Co., Ltd.

The O/W wrinkle care cream of Formulation Example 4 was prepared by the following procedures.
1. Mix phase A until uniform.
2. While stirring phase B, slowly add the product from step 1.
3. Add the product from step 2 to phase C and mix until uniform.

Formulation Example 5: Compact Foundation (Ingredients)
Phase A
1) Cyclopentasiloxane, Cyclohexasiloxane (Note 1): 4 parts by mass
2) Cetyl dimethicone (Note 2): 2 parts by mass
3) Stearyl dimethicone (Note 3): 6 parts by mass
4) Alkyl (C30-45) methicone, Olefin (C30-45) (Note 4): 3 parts by mass
5) Beeswax (Note 5): 8 parts by mass
6) Cyclopentasiloxane, polypropylsilsesquioxane (Note 6): 5 parts by mass
7) Preservative: 0.5 parts by mass
Phase B
8) Cyclopentasiloxane (Note 7): 44 parts by mass
9) Red iron oxide (Note 8): 1.5 parts by mass
10) Yellow iron oxide (Note 9): 2.5 parts by mass
11) Black iron oxide (Note 10): 0.75 parts by mass
12) Brown iron oxide (Note 11): 5.75 parts by mass
Phase C
13) Silica (Note 12): 1 part by mass
14) Silicone crosslinked body of the example: 6 parts by mass
15) Corn starch A1 octenylsuccinate (Note 13): 4 parts by mass
16) Talc: 2 parts by mass
17) Allantoin (Note 14): 1 part by mass
18) Titanium oxide (Note 15): 3 parts by mass
Note 1: DC 345 manufactured by Dow Corning Toray
Note 2: 2502 COSMETIC FLUID manufactured by Dow Corning Toray
Note 3: 2503 COSMETIC WAX manufactured by Dow Corning Toray
Note 4: AMS-C30 COSMETIC WAX manufactured by Dow Corning Toray
Note 5: Cerabeil White No. 1 manufactured by Baerlocher France S.A.
Note 6: 670 FLUID manufactured by Dow Corning Toray
Note 7: SH 245 manufactured by Dow Corning Toray
Note 8: Unipure Red LC 381 AS-EM manufactured by Sensient Cosmetic Technologies
Note 9: Unipure Yellow LC 182 AS-EM manufactured by Sensient Cosmetic Technologies
Note 10: Unipure Black LC 989 AS-EM manufactured by Sensient Cosmetic Technologies
Note 11: Unipure Brown LC 881 manufactured by Sensient Cosmetic Technologies
Note 12: LDP 1500 manufactured by Sensient Cosmetic Technologies
Note 13: Dry Flo Plus manufactured by National Starch & Chemical Company
Note 14: Allantoin/ISP
Note 15: Matlake OPA-AS manufactured by Sensient Cosmetic Technologies The compact foundation of Formulation Example 5 was prepared using the following procedures.
1. Heat phase A to 80° C. to dissolve.
2. Mix the ingredients 9 to 12 until uniform.
3. Disperse the product from step 2 in the ingredient 8.
4. Mix phase C until uniform.
5. Mix the product from step 3 and the product from step 4.
6. While stirring the product from step 1, add the product from step 5 and stir together (80° C.).
7. Transfer to a container and solidify by cooling.

Formulation Example 6: Antiperspirant (Ingredients)
Phase A
1) Cetyl diglycerl tris(trimethylsiloxy) silylethyl dimethicone (Note 1): 2 parts by mass
2) Dimethicone (Note 2): 10 parts by mass
3) Silicone crosslinked body from the example: 2 parts by mass
4) Phenyl trimethicone (Note 3): 4 parts by mass
Phase B
5) Octachlorohydrex glycine (Al/zirconium), water (Note 4): 45 parts by mass
6) Glycerin: 5.5 parts by mass
7) Propanediol: 12.5 parts by mass
8) Pure water: 18.5 parts by mass
9) Preservative: 0.5 parts by mass
Note 1: ES-5600 SILICONE GLYCEROL EMULSIFIER manufactured by Dow Corning Toray
Note 2: SH200C FLUID 2CS manufactured by Dow Corning Toray
Note 3: 556 FLUID manufactured by Dow Corning Toray
Note 4: Reach AZO 956G manufactured by Summit Reheis The antiperspirant from Formulation Example 6 was prepared according to the following procedures.
1. Mix phase A until uniform.
2. Mix Phase B until uniform.

3. While stirring the product from step 1, perform emulsification by slowly adding the product from step 2.

Formulation Example 7: Hair Oil (Ingredients)
1) Cyclopentasiloxane (Note 1): 45 parts by mass
2) Silicone crosslinked body from the example: 2.7 parts by mass
3) Caprylyl methicone (Note 2): 20 parts by mass
4) Argan oil: 0.1 parts by mass
5) Olive oil: 0.1 parts by mass
6) Phenyl trimethicone (Note 3): 2 parts by mass
7) Cyclopentasiloxane, dimethiconol (Note 4): 30 parts by mass
8) Perfume: 0.1 parts by mass
Note 1: SH 245 manufactured by Dow Corning Toray
Note 2: SS-3408 manufactured by Dow Corning Toray
Note 3: 556 FLUID manufactured by Dow Corning Toray
Note 4: PMX-1501 Fluid manufactured by Dow Corning Toray The hair oil of Formulation Example 7 was prepared using the following procedures.
1. Disperse the ingredient 2 in the ingredient 1.
2. Add and mix the remaining ingredients 3 to 8 to the product from step 1.

INDUSTRIAL APPLICABILITY

The cured silicone particles of the present invention can easily be blended as an additive since the cured silicone particles have excellent dispersibility to ethanol and silicone oil, and can be used for a skin cosmetic material, make up cosmetic material, or the like because the feeling thereof can be improved when blended to cosmetic material as a cosmetic raw material. Furthermore, the physical properties of the cured silicone particles of the present invention can be fully utilized, and the particles can be used as an additive for a thermosetting resin composition, a thermoplastic resin composition, and the like, or in a surface lubricant for plastic film.

The invention claimed is:

1. Cured silicone particles obtained by curing a curable silicone composition comprising at least the following components (A) through (C), wherein the average particle size of the cured silicone particles is from 0.1 to 500 μm:

(A) a polyorganosiloxane expressed by the average formula:

$$[R^a R^b_2 SiO(R^b_2 SiO)_n]_4 Si$$

where n is a number that is 0 or greater, however, in one molecule, at least one n is a number that is 1 or greater; each $R^a$ may be the same or different and is selected from an alkyl group with 1 to 6 carbon atoms, or an alkenyl group with 2 to 12 carbon atoms, however, in one molecule, at least two $R^a$ are alkenyl groups; and each $R^b$ may be the same or different and is selected from an alkyl group with 1 to 6 carbon atoms, an alkenyl group with 2 to 12 carbon atoms, or an aryl group with 6 to 20 carbon atoms;

(B) (B-1) a polyorganosiloxane expressed by the average unit formula:

$$(R^c_3 SiO_{1/2})_p (R^c_2 SiO_{2/2})_q (R^d SiO_{3/2})_r$$

where each $R^c$ may be the same or different and is selected from a hydrogen atom, an alkyl group with 1 to 6 carbon atoms, or an aryl group with 6 to 20 carbon atoms, however, in one molecule, at least two $R^c$ are hydrogen atoms; and each $R^d$ may be the same or different and is selected from an alkyl group with 1 to 6 carbon atoms, or an aryl group with 6 to 20 carbon atoms, and p, q, and r are all individually selected numbers that are greater than 0 and that satisfy the equation p+q+r=1; and/or (B-2) a polyorganosiloxane expressed by the average formula:

$$HR^d_2 SiO(R^d_2 SiO)_m SiR^d_2 H$$

where m is a number greater than 0, and $R^d$ is the same as described in (B-1); and (C) a catalyst for a hydrosilylation reaction.

2. The cured silicone particles according to claim 1, wherein the curable silicone composition for obtaining the cured silicone particles further comprises (D) a polyorganosiloxane expressed by the average formula:

$$R^e R^d_2 SiO(R^d_2 SiO)_k SiR^d_2 R^e$$

where each $R^e$ is an independently selected alkenyl group with 2 to 12 carbon atoms, each $R^d$ is independently selected and defined as in claim 1, and k is a number greater than 0.

3. A method of manufacturing the cured silicone particles according to claim 1, comprising:
preparing fine particles from a mixture of component (A) and component (B),
blending component (C) and the fine particles to prepare fine particles of a curable silicone composition, and
curing the curable silicone composition to give the cured silicone particles.

4. A method of manufacturing the cured silicone particles according to claim 1, comprising:
mixing component (A), component (B), and component (C) to form a curable silicone composition,
producing fine particles of the curable silicone composition, and
curing the curable silicone composition to give the cured silicone particles.

5. A cosmetic raw material obtained by dispersing the cured silicone particles according to claim 1 in a water-based solvent or an oil-based solvent.

6. A cosmetic material comprising the cured silicone particles according to claim 1.

7. The cosmetic material according to claim 6, which is a cosmetic material for skin.

8. The cosmetic material according to claim 7, which is a makeup cosmetic material or sunscreen agent.

9. A method of preparing cured silicone particles, said method comprising:
forming a curable silicone composition,
producing fine particles of the curable silicone composition, and
curing the curable silicone composition to give the cured silicone particles;
wherein the curable silicone composition comprises at least the following components (A) through (C),
(A) a polyorganosiloxane expressed by the average formula:

$$[R^a R^b_2 SiO(R^b_2 SiO)_n]_4 Si$$

where n is a number that is 0 or greater, however, in one molecule, at least one n is a number that is 1 or greater; each $R^a$ may be the same or different and is selected from an alkyl group with 1 to 6 carbon atoms, or an alkenyl group with 2 to 12 carbon atoms, however, in one molecule, at least two $R^a$ are alkenyl groups; and each $R^b$ may be the same or different and is selected from an alkyl group with 1 to 6 carbon atoms, an alkenyl group with 2 to 12 carbon atoms, or an aryl group with 6 to 20 carbon atoms;

(B) (B-1) a polyorganosiloxane expressed by the average unit formula:

$$(R^c{}_3SiO_{1/2})_p(R^c{}_2SiO_{2/2})_q(R^dSiO_{3/2})_r$$

where each $R^c$ may be the same or different and is selected from a hydrogen atom, an alkyl group with 1 to 6 carbon atoms, or an aryl group with 6 to 20 carbon atoms, however, in one molecule, at least two $R^c$ are hydrogen atoms; and each $R^d$ may be the same or different and is selected from an alkyl group with 1 to 6 carbon atoms, or an aryl group with 6 to 20 carbon atoms, and p, q, and r are all individually selected numbers that are greater than 0 and that satisfy the equation p+q+r=1; and/or (B-2) a polyorganosiloxane expressed by the average formula:

$$HR^d{}_2SiO(R^d{}_2SiO)_mSiR^d{}_2H$$

where m is a number greater than 0, and $R^d$ is the same as described in (B-1); and (C) a catalyst for a hydrosilylation reaction.

10. The method of claim 9, wherein forming the curable silicone composition comprises mixing component (A), component (B), and component (C).

11. The method of claim 9, wherein forming the curable silicone composition comprises preparing fine particles from a mixture of component (A) and component (B), and blending component (C) and the fine particles.

12. The method of claim 9, wherein the curable silicone composition further comprises (D) a polyorganosiloxane expressed by the average formula:

$$R^eR^d{}_2SiO(R^d{}_2SiO)_kSiR^d{}_2R^e$$

where each $R^e$ is an independently selected alkenyl group with 2 to 12 carbon atoms, each $R^d$ is independently selected and defined as in claim 9, and k is a number greater than 0.

13. A method of preparing a cosmetic raw material, said method comprising:
forming a curable silicone composition,
producing fine particles of the curable silicone composition,
curing the curable silicone composition to give the cured silicone particles; and
dispersing the cured silicone particles in a water-based solvent or an oil-based solvent to give the cosmetic raw material;
wherein the curable silicone composition comprises at least the following components (A) through (C), (A) a polyorganosiloxane expressed by the average formula:

$$[R^aR^b{}_2SiO(R^b{}_2SiO)_n]_4Si$$

where n is a number that is 0 or greater, however, in one molecule, at least one n is a number that is 1 or greater; each $R^a$ may be the same or different and is selected from an alkyl group with 1 to 6 carbon atoms, or an alkenyl group with 2 to 12 carbon atoms, however, in one molecule, at least two $R^a$ are alkenyl groups; and each $R^b$ may be the same or different and is selected from an alkyl group with 1 to 6 carbon atoms, an alkenyl group with 2 to 12 carbon atoms, or an aryl group with 6 to 20 carbon atoms;

(B) (B-1) a polyorganosiloxane expressed by the average unit formula:

$$(R^c{}_3SiO_{1/2})_p(R^c{}_2SiO_{2/2})_q(R^dSiO_{3/2})_r$$

where each $R^c$ may be the same or different and is selected from a hydrogen atom, an alkyl group with 1 to 6 carbon atoms, or an aryl group with 6 to 20 carbon atoms, however, in one molecule, at least two $R^c$ are hydrogen atoms; and each $R^d$ may be the same or different and is selected from an alkyl group with 1 to 6 carbon atoms, or an aryl group with 6 to 20 carbon atoms, and p, q, and r are all individually selected numbers that are greater than 0 and that satisfy the equation p+q+r=1; and/or (B-2) a polyorganosiloxane expressed by the average formula $$HR^d{}_2SiO(R^d{}_2SiO)_mSiR^d{}_2H$$

where m is a number greater than 0, and $R^d$ is the same as described in (B-1); and (C) a catalyst for a hydrosilylation reaction.

* * * * *